United States Patent [19]

Robotti et al.

[11] Patent Number: 5,462,991
[45] Date of Patent: Oct. 31, 1995

[54] IMMOBILIZATION OF PH-SENSITIVE DYES TO SOLID SUPPORTS

[76] Inventors: Karla M. Robotti, 1008 Gull Ave., Foster City, Calif. 94404; Carl A. Myerholtz, 18644 Loree Ave., Cupertino, Calif. 95014

[21] Appl. No.: 293,870

[22] Filed: Aug. 22, 1994

Related U.S. Application Data

[62] Division of Ser. No. 718,062, Jun. 20, 1991, Pat. No. 5,384,411.

[51] Int. Cl.[6] .................... C07D 327/01; C07D 307/78; C07D 307/92
[52] U.S. Cl. .................... 525/54.3; 525/54.31; 525/218; 525/474; 436/523; 436/524; 436/527; 436/528; 436/529; 436/530; 436/531
[58] Field of Search .................... 525/54.3, 54.31, 525/218, 474; 436/523, 524, 527, 528, 529, 530, 531

[56] References Cited

U.S. PATENT DOCUMENTS 4,134,936  1/1979  Byrne et al. ............................ 260/860
4,595,733  6/1986  Tyrell et al. ............................ 525/462

*Primary Examiner*—Nathan M. Nutter

[57] ABSTRACT

Disclosed are pH dyes containing a suitable compatible substituent which permits binding of the dye to a solid support. Also disclosed are methods for synthesizing such dyes prior to their coupling to the solid supports.

19 Claims, No Drawings

IMMOBILIZATION OF PH-SENSITIVE DYES TO SOLID SUPPORTS

CROSS RELATED TO RELATED APPLICATIONS

This is a divisional of application Ser. No. 07/718,062 filed on 20 Jun. 1991, and now U.S. Pat. No. 5,384,411.

BACKGROUND OF THE INVENTION

1. Field of the Invention

The present invention is directed to pH dyes containing a suitable compatible substituent which permits binding to a solid support as well as to solid supports containing such bound dyes. The present invention is also directed to methods for synthesizing such dyes prior to their coupling to the solid supports.

2. State of the Art

The binding of biologically or chemically active components to solid supports is well known in the art. For example, in the field of medical diagnostics, it is common to bind a biologically active component (e.g., an antigen or an antibody) to a solid support for use in a diagnostic assay. The binding of such components facilitates reagent interaction and/or separation.

In the field of analytical chemistry, the binding of a chemically active component to a solid support such as a probe has been suggested as a means of permitting the solid phase incorporation of the component. Such solid phase incorporation eliminates the possibility that the component will leach from the probe when contacted with the intended environment. In this regard, Posch et al., Fresenius Z Anal. Chem., Vol. 334, pp. 162–165 (1989), disclose the binding of fluorescent compounds such as fluorescein to solid supports useful in fibre optics. The fluorescent compound is used in a method to determine the pH of the a solution between the pHs of 0 to 7.

The binding of a fluorescent component, such as fluorescein, rhodamine, etc., to a solid support is facilitated because such components contain one or more reactive functionalities (e.g., amine, hydroxyl, or carboxyl functionalities) which permit the covalent linking of these compounds to a solid support. However, the use of a solid support containing a fluorescent component in fibre optics is complicated by the fact that while most commercially available fibre optics poorly transmit short wavelength light, such short wavelength light is generally employed to excite the fluorescent moiety. Moreover, fluorescent methods are further complicated by problems of quenching and dye photodegradation. Additionally, problems can arise because the binding of the fluorescent component to the solid support can result in significant chemical changes in the bound fluorescent component as compared to the unbound component and these changes can interfere with the intended use of the component. For example, Posch et al., supra, states that upon binding of Rhodamine B to the solid support, there was a strong $pK_a$ shift in the bound component as compared to the unbound component.

On the other hand, certain phthalein type dyes are well known pH indicators. When incorporated into an aqueous solution, these dyes provide for protonated or unprotonated species and depending on the degree of protonation, will produce solutions of different colors or color intensity. When the pH value of a solution produces a color in the presence of the pH indicator, the extent of protonation of the indicator and hence the pH of the solution can be correlated to the intensity of the color of the solution.

However, in solid phase pH sensors, the use of such well known pH dyes as substitutes for fluorescent indicators has not been heretofore possible because such dyes lack suitable functionality which would permit the covalent binding of the dye to the solid support without interfering with the pH sensitivity of the dye. Moreover, it is uncertain as to whether the incorporation of such functionality into the dye would not alter the chemical properties of the dye.

SUMMARY OF THE INVENTION

The present invention is directed to the discovery that the incorporation of compatible reactive functionalities into the appropriate sites on certain phthalein type pH dyes permit the binding of these dyes onto solid supports without interfering with the pH sensitivity of the dyes. The resulting dye-containing solid supports can then be employed as non-leaching solid phase pH indicators in such uses as fibre optic pH sensors.

Accordingly, in one of its composition aspects, the present invention is directed to dyes containing compatible reactive functionalities which permit the binding of these dyes onto solid supports. The functionalized dyes of this invention are represented by the formula I–III:

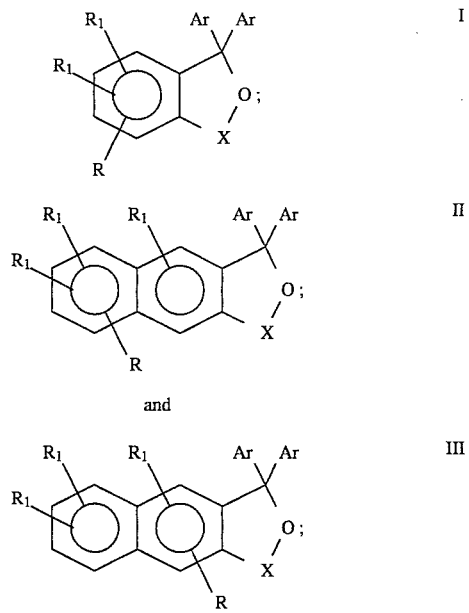

wherein R is a compatible functional group or a compatible linked functional group capable of forming a stable covalent bond with a solid support; each $R_1$ is independently hydrogen or a compatible substituent; each Ar is independently a 4-hydroxyphenyl or 4-hydroxynapthyl group having from 0 to 3 compatible substituents selected from the group consisting of alkyl of from 1 to 6 carbon atoms, halo and nitro; and X is >C=O or >SO$_2$.

Preferably, R is selected from the group consisting of hydroxyl, carboxyl, amino (including —NH$_2$ and —NHR$_3$), R$_2$—OH, R$_2$—COOH, and R$_2$—NH$_2$ wherein R$_2$ is compatible linker group and R$_3$ is hydrocarbyl of from about 1 to 10 carbon atoms. In another preferred embodiment, each $R_1$ is hydrogen. However, when $R_1$ is a compatible substituent, this substituent is preferably a compatible substituent selected from the group consisting of alkyl of from 1 to 6 carbon atoms, and alkoxy of from 1 to 61 carbon atoms.

The present invention is also directed to a solid support having one or more dye substituents covalently bound thereto. Such solid supports are represented by formula IV, V and VI:

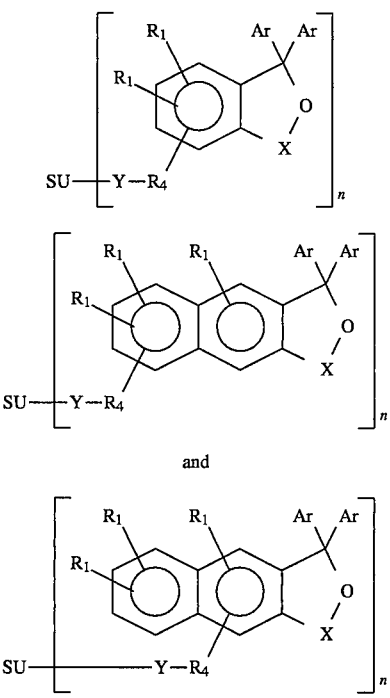

wherein each $R_1$ is independently hydrogen or a compatible substituent; $R_4$ is a bond or a compatible linker group; SU is a solid support; Y is the residue of the reactive functionality attached to $R_4$ and which forms a stable covalent bond with the solid support; each Ar is independently a 4-hydroxyphenyl or 4-hydroxynaphthyl group having from 0 to 3 compatible substituents selected from the group consisting of alkyl, halo and nitro and n is an integer equal to at least 1 and preferably an integer from 1 to about 100.

In one of its process aspects, the present invention is directed to a process for the preparation of compounds of the formula VII:

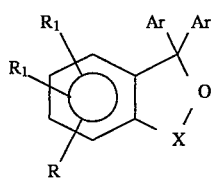

wherein R is a compatible functional group or a compatible linked functional group capable of forming a stable covalent bond with a solid support; each $R_1$ is independently hydrogen or a compatible substituent; each Ar is independently a 4-hydroxyphenyl or 4-hydroxynapthyl group having from 0 to 3 compatible substituents selected from the group consisting of alkyl of from 1 to 6 carbon atoms, halo and nitro; and X is either $>C=O$ or $>S(O)_2$; which method comprises combining a compound of the formula VIII:

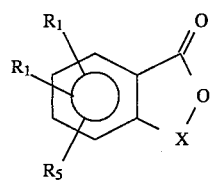

with at least 2 molar equivalents of a phenol or 1-naphthol having from 0 to 3 compatible substituents selected from the group consisting of alkyl of from 1 to 6 carbon atoms, halo and nitro and with the proviso that there are no such substituents at the 4 position of the phenol and the 1-naphthol, and under conditions sufficient so as to form a compound of the formula IX:

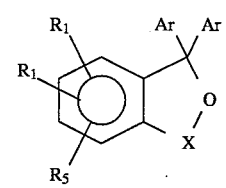

wherein Ar and $R_1$ is as defined above and $R_5$ is selected from the group consisting of a compatible functional group or a compatible linked functional group capable of forming a stable covalent bond with a solid support, and a group capable of being derivatized to either a compatible functional group or a compatible linked functional group; and when $R_5$ is a group capable of being derivatized to either a compatible functional group or a compatible linked functional group, said $R_5$ group is derivatized under conditions sufficient to convert this group to either a compatible functional group or a compatible linked functional group so as to produce a compound of formula VII.

In another of its process aspects, the present invention is directed to a process for the preparation of compounds of the formula X or XI:

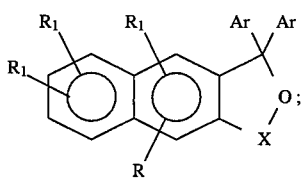

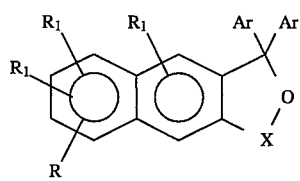

wherein R is a compatible functional group or a compatible linked functional group capable of forming a stable covalent bond with a solid support; each $R_1$ is independently hydrogen or a compatible substituent; each Ar is independently a 4-hydroxyphenyl or 4-hydroxynapthyl group having from 0 to 3 compatible substituents selected from the group consisting of alkyl of from 1 to 6 carbon atoms, halo and nitro; which method comprises combining a compound of either formula XII or XIII:

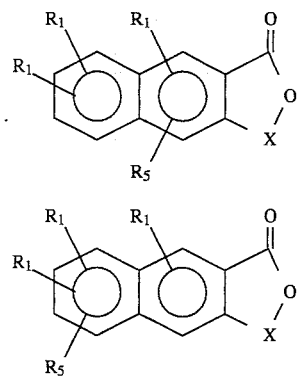

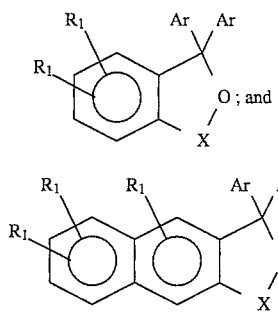

with at least 2 molar equivalents of a phenol or 1-naphthol having from 0 to 3 compatible substituents selected from the group consisting of alkyl of from 1 to 6 carbon atoms, halo and nitro and with the proviso that there are no such substituents at the 4 position of the phenol and the 1-naphthol, and under conditions sufficient so as to form a compound of either the formula XIV or XV:

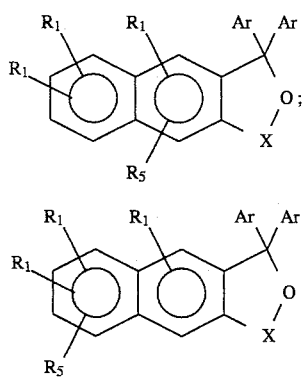

wherein Ar and $R_1$ are as defined above and $R_5$ is selected from the group consisting of a compatible functional group or a compatible linked functional group capable of forming a stable covalent bond with a solid support, and a group capable of being derivatized to either a compatible functional group or a compatible linked functional group; and when $R_5$ is a group capable of being derivatized to either a compatible functional group or a compatible linked functional group, said $R_5$ group is derivatized under conditions sufficient to convert this group to either a compatible functional group or a compatible linked functional group so as to produce a compound of either formula X or XI.

DETAILED DESCRIPTION OF THE INVENTION

As noted above, the present invention is directed in part to pH dyes containing a suitable compatible substituent which permits binding to a solid support as well as to solid supports containing such bound dyes. The present invention is also directed to methods for synthesizing such dyes prior to their coupling to solid supports. However, prior to discussing this invention in further detail, the following terms will first be defined.

As used herein, the term "pH dye" refers to compounds of the formula XVI and XVII wherein $R_1$, Ar and X are as defined above. Such pH dyes are water soluble and are art recognized to be useful as pH indicators insofar as these compounds will change their color based on the concentration of hydrogen ions in an aqueous solution. Specifically, the hydroxyl groups of the Ar moieties of these dyes are acidic and therefore will deprotonate under sufficiently basic conditions. Upon deprotonation, the dye will become basic and the color of the basic dye is different relative to the acidic dye and this difference is readily detectable. Deprotonation of these dyes is governed by the $pK_a$ of the dye and the actual pH of the solution. Thus, knowledge of the $pK_a$ of a specific dye coupled with knowledge of the intensity of the color of the solution permits the skilled artisan to determine the pH of the solution with a high degree of accuracy within about ±1 pH unit of the $pK_a$ of the compound. Additionally, because the $pK_a$ of the dye is governed by the substituents attached thereto, it is possible to generate a series of dyes having different $pK_a$'s merely by changing one or more of the substituents, particularly the substituents on either or both of the Ar moieties found on the dye.

The term "stable covalent bond" refers to a covalent bond which is substantially stable (i.e., greater than 95% stability and preferably greater than 99% stability) at 40° C. in an aqueous medium maintained within a suitable pH range for a period of at least 0.5 minutes. Preferably, the covalent bond is substantially stable under these conditions for a period of at least 20 minutes and more preferably for a period of at least 1 hour. Suitably stable covalent bonds for use herein include amide bonds [>NC(O)—], ether bonds, carbamate bonds [>NC(O)O—], urea bonds [>NC(O)N<], and the like.

The particular stable covalent bond employed to link the functionalized dye to the support is not critical provided that it is stable at the pH range intended to be measured. In this regard, it is noted that some covalent bonds may be stable at one pH range and unstable at another (e.g., esters). Accordingly, when such covalent bonds are employed, these bonds are stable covalent bonds for the purposes herein only when employed at a suitable pH range, i.e., one which permits the bond to remain at least 95% stable under the conditions described above. The selection of a suitably stable covalent bond for a given pH range is within the skill of the art. Because of its ease of preparation as well as its relative stability over a range of pH's, a particularly preferred covalent bond for use in this invention is an amide bond [>NC(O)—].

The term "solid support" refers to any solid support which contains surface reactive groups or can be derivatized so as to contain surface reactive groups which can react with the functional group on the dye so as to form a stable covalent bond. Suitable solid supports include SEPHAROSE™ (agarose gel), aminopropyl-silica, aminopropyl-CPG (controlled pore glass), aminoethyl cellulose, TRISACRYL®-NH (a copolymer with a polyethylene core with aminoethyl groups on the surface) glass beads, polyacrylamide particles, and the like. Such supports are either commercially available or can be prepared using conventional methodology.

In this regard, sepharose, aminopropyl-silica, aminopropyl-CPG (controlled pore glass), aminoethyl cellulose, TRISACRYL®-NH, contain reactive surface groups and do not need to be surface functionalized in order to be reactive with a suitable functional group on the dye. On the other hand, glass beads can be derivatized via silanization so as to be capable of forming a stable covalent bond with a suitable functional group on the dye. See Weetal, U.S. Pat. No. 3,652,761, which is incorporated herein by reference. Likewise, polyacrylamide can be hydrolyzed so as to provide particles of defined size having reactive functionalities on the surface thereof. See Blakemore et al., U.S. Pat. No. 4,088,746, which is incorporated herein by reference.

The particular solid support to which the functionalized dye is attached is not critical provided that it is stable at the pH range intended to be measured. In this regard, it is noted that some solid supports may be stable at one pH range and unstable at another (e.g., polyacrylamide hydrolyzes at high pH). Accordingly, the solid support is selected relative to the conditions in which the support is intended for use.

The term "compatible functional group capable of forming a stable covalent bond" refers to those groups which are compatible with the dye to which they are bound and which can react with a substituent on the solid support so as to form a stable covalent bond. In regard to the above, compatible functional groups are those groups which do not alter the pH indicating ability of the dye. Thus, for example, while a particular functional group may alter the specific pH at which the hydroxyl groups of the dye are protonated/deprotonated, such functional groups are deemed compatible if the resulting dye can still be used as a pH indicator at some pH range. Obviously, if attachment of a particular functional group so alters the characteristics of the dye so as to render the resulting dye incapable of being used as a pH indicator at any pH range, then the functional group would be deemed incompatible.

Suitable compatible functional groups include, by way of example, carboxylic acid groups (including activated esters and mixed anhydrides thereof), amine groups (including primary and secondary amines), hydroxyl groups, and the like.

The term "compatible linked functional group capable of forming a stable covalent bond" refers to those groups which are compatible with the dye to which they are bound and which contain one or more functional groups which are attached to the dye via a linking group and which functional group(s) can react with a substituent on the solid support so as to form a stable covalent bond. In regard to the above, compatible linked functional groups are those groups which do not alter the pH indicating ability of the dye. Thus, for example, while a particular linked functional group may alter the specific pH at which the hydroxyl groups of the dye are protonated/deprotonated, such linked functional groups are deemed compatible if the resulting dye can still be used as a pH indicator at some pH range. Obviously, if attachment of a particular linked functional group so alters the characteristics of the dye so as to render the resulting dye incapable of being used as a pH indicator at any pH range, then the linked functional group would be deemed incompatible.

Suitable compatible linked functional groups contain one or more reactive functionalities such as, by way of example, carboxylic acid groups (including activated esters and mixed anhydrides thereof), amine groups (including primary and secondary amines), hydroxyl groups, unsaturated aliphatic groups, and the like. The reactive functionality(ies) are attached to the dye via a linking group. The particular linking group employed is not critical provided that it is compatible with the dye and includes linking groups such as hydrocarbyl linking groups of from 1 to about 10 carbon atoms, carbonylhydrocarbyl linking groups of from 1 to about 10 carbon atoms and the like.

Preferred compatible linked functional groups are represented by the formula:

$$-[C(O)]_p(NR_6)_q R_7 - (Z)_s$$

wherein p is an integer equal to zero or one; q is an integer equal to zero or one; $R_6$ is hydrogen or a hydrocarbyl group of from 1 to about 10 carbon atoms; $R_7$ is a hydrocarbyl group of from 1 to about 10 carbon atoms; Z is a reactive functionality selected from the group consisting of carboxylic acid groups (including activated esters and mixed anhydrides thereof), amine groups (including primary and secondary amines), hydroxyl groups, unsaturated aliphatic groups, epoxides and the like; and s is an integer equal to at least 1.

Hydrocarbyl, as used in describing the linker groups of this invention, refer to an organic radical composed of carbon and hydrogen which may be aliphatic, alicyclic, aromatic or combinations thereof, e.g., aralkyl. Particularly preferred hydrocarbyl groups are alkyl or alkylene groups of from 1 to about 6 carbon atoms.

The term "compatible substituent" refers to those substituents which do not alter the pH indicating ability of the dye. Thus, for example, while a particular substituent may alter the specific pH at which the hydroxyl groups of the dye are protonated/deprotonated, such substituents are deemed compatible if the resulting dye can still be used as a pH indicator at some pH range. Obviously, if attachment of a particular substituent or a combination of substituents so alters the characteristics of the dye so as to render the resulting dye incapable of being used as a pH indicator at any pH range, then such a substituent would be deemed incompatible.

The surface reactive groups on the solid support are chosen relative to the reactive functionalities attached to the dye. Thus, in the case where the reactive functionality of the dye is a carboxylic acid group (including an activated ester or mixed anhydride thereof), the surface reactive group of the solid support is generally selected to an amine so when reactively combined, a covalent amide bond will result. Similarly, when the reactive functionality of the dye is an amine, the surface reactive group of the solid support is generally an epoxide, a carboxylic acid (including an activated ester thereof or a mixed anhydride), and the like.

The functionalized dyes of this invention are prepared in one of two methods. The first method employs an appropriately substituted phthalic anhydride or 2,3-naphthlenic anhydride which is reacted as depicted below so as to form a suitable dye (wherein X is >C=O). In these depicted reactions, an appropriately substituted phthalic anhydride is employed for illustrative purposes only and an appropriately substituted 2,3-naphthlenic anhydride can also be employed in these reactions and will react similarly.

Specifically, in the first method, a suitably substituted phthalic anhydride, XVIII, is combined with compound XIX (which is phenol and/or 1-naphthol having from 0 to 3 compatible substituents selected from the group consisting of alkyl of from 1 to 6 carbon atoms, halo and nitro and with the proviso that there are no such substituents at the 4 position of the phenol and the 1-naphthol) and contacted under conditions sufficient to result in the fusion of the phenol and/or 1-napthol compounds to the phthalic anhydride as shown in reaction (1) below [In reaction (1), Ar—H, Compound XIX, reflects phenol and/or 1-naphthol compounds having a hydrogen substituent at the 4-position as defined above]: t,0180 wherein Ar and $R_1$ is as defined above and $R_5$ is selected from the group consisting of a compatible functional group or a compatible linked functional group capable of forming a stable covalent bond with a solid support and a group capable of being derivatized to either a compatible functional group or a compatible linked functional group.

Specifically, reaction (1) is conducted by combining at least 2 molar equivalents of compound XIX with phthalic anhydride XVIII at an elevated temperature of from about 40° C. to about 250° C. In general, the reaction also employs a catalytic amount (generally about 5 to about 20 wt. % and preferably about 13 wt. % based on the total weight of the starting materials) of a suitable fusion catalyst such as $ZnCl_2$, $H_2SO_4$, $SnCl_4$, and the like. The reaction is generally conducted neat and is generally complete in from about 0.1 to about 2 hours. Afterwards, the product XX may be further isolated by conventional techniques such as stripping, chromatography, filtration, and the like.

The phthalic anhydrides of formula XVIII as well as 2,3-naphthenic anhydrides are either commercially available or can be prepared by art recognized methods. For example, 1,2,4-benzenetricarboxylic acid, 3-nitrophthalic anhydride, and 4-nitrophthalic anhydride are commercially available from Aldrich. Likewise, the phenol and 1-naphthol compounds (compound XIX) are either commercially available or can be prepared by art recognized methods.

The second method employs an optionally substituted 4-carboxy-o-sulfobenzoic anhydride, XXI, or a corresponding naphthalene compound (i.e., X is $>S(O)_2$) which is reacted as described below so as to form a suitable dye. In these depicted reactions, an optionally substituted 4-carboxy-o-sulfobenzoic anhydride is employed for illustrative purposes only and a corresponding naphthalene compound can also be employed in these reactions and will react similarly.

Specifically, in the second method, an optionally substituted 4-carboxy-o-sulfobenzoic anhydride, XXI, is combined with compound XIX (which is phenol and/or 1-naphthol having from 0 to 3 compatible substituents selected from the group consisting of alkyl of from 1 to 6 carbon atoms, halo and nitro and with the proviso that there are no such substituents at the 4 position of the phenol and the 1-naphthol) and contacted under conditions sufficient to result in the fusion of the phenol and/or 1-napthol compounds to sulfobenzoic anhydride as shown in reaction (2) below [In reaction (2), Ar—H, Compound XIX, reflects phenol and/or 1-naphthol compounds having a hydrogen substituent at the 4-position as defined above]:

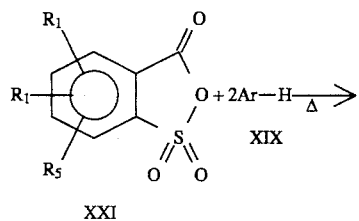

XXI

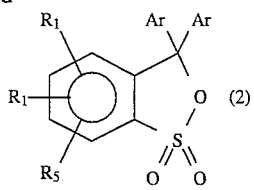

XXII wherein Ar and $R_1$ is as defined above and $R_5$ is selected from the group consisting of a compatible functional group or a compatible linked functional group capable of forming a stable covalent bond with a solid support and a group capable of being derivatized to either a compatible functional group or a compatible linked functional group.

In particular, reaction (2) is conducted by combining at least 2 molar equivalents of compound XIX with 4-carboxy-o-sulfobenzoic anhydride, XXI, at an elevated temperature of from about 40° C. to about 250° C. In general, the reaction also employs a catalytic amount (generally from about 5 wt. % to about 20 wt. % and preferably about 13 wt. % based on the total weight of the starting materials) of a suitable fusion catalyst such as $ZnCl_2$, $H_2SO_4$, $SnCl_4$, and the like. The reaction is conducted neat and is generally complete in from about 0.1 to about 2 hours. Afterwards, the product may be further isolated by conventional techniques such as stripping, chromatography, filtration, and the like.

The 4-substituted-o-sulfobenzoic anhydride of formula XXI as well as 2,3-naphthenic anhydrides are generally prepared from a suitably substituted benzoic acid or 2-naphthoic acid. Specifically, an appropriately 4-substituted benzoic or an appropriately substituted 2-naphthoic acid is contacted with fuming sulfuric acid ($H_2SO_4$) in the presence of mercury at an elevated temperature of from about 200°–300° C. so as to sulfonate ortho to the carboxyl group. Insofar as carboxyl groups are meta directing as they relate to sulfonation reactions, the substituent(s) on the benzoic acid or on the 2-naphthoic acid should be sufficiently electron withdrawing so as to force sulfonation ortho to the carboxyl group. For example, if terephthalic acid is employed, then by necessity monosulfonation must occur at a position ortho to one of the carboxylic acid group. Other electron withdrawing substituents include for example, nitro, cyano, —C(O)H and the like. After sulfonation, the anhydride is formed merely by contacting the 2-sulfobenzoic acid or the 3-sulfo-2-naphthoic acid with a dehydrating agent such as acetic anhydride at elevated temperatures (e.g., about 100° C.) for a sufficient period of time (e.g., about 4 hours) to effect anhydride formation.

In formula XX and XXII (or in the corresponding naphthalene analogue), if $R_5$ is either a compatible functional group or a compatible linked functional group capable of forming a stable covalent bond with a solid support, these dyes can then be used directly in the coupling reaction described below. On the other hand, if $R_5$ is a group capable of being derivatized to either a compatible functional group or a compatible linked functional group, then it is necessary to derivatize this functionality prior to use in the coupling reaction. For example, if $R_5$ is nitro or a nitro group attached to a linking arm, then prior to coupling the dye to the solid support, the nitro group is reduced to an amino group preferably under conditions which do not affect other groups or substituents on the dye. Derivatization of other groups, including compatible functional groups, to either a compatible functional group or a compatible linked functional group is well known in the art. For example, it is possible to react a carboxylic acid functional group (including its activated ester and mixed anhydride) with ethylene diamine or other polyamine, so as to convert the carboxylic acid group to a —C(O)NHCH$_2$CH$_2$NH$_2$ group which contains a reactive functionality (—NH$_2$) connected to a linking arm (—C(O)CH$_2$CH$_2$—). The resulting dyes are represented by formula I, II and III above.

The dyes of formula I, II and III are then coupled to an appropriately functionalized solid support. This coupling reaction is conducted by employing complimentary reactive functionalities on the dye and on the solid support. That is to say that the surface reactive group employed on the solid support is one which is reactive with the functional group on the dye so as to form a stable covalent bond. For example, if an amine group is employed as the surface reactive group on the solid support, then the functional group on the dye should be a group which is reactive with an amine (e.g., a carboxylic acid or its activated ester or mixed anhydride). Such coupling reactions are well known in the art and are described in, for example, Weetall, U.S. Pat. No. 3,652,761 (glass beads), Blakemore et al., U.S. Pat. No. 4,088,476 (polyacrylamide particles), and the like.

The coupling reaction results in the loss or conversion of part of the functional group on the dye. For example, if the functional group is a carboxyl group which is reacted with an amine, then the resulting amide will have only the residual carbonyl group from the carboxyl functional group on the dye. In these circumstances, the —OH group of the functional group attached to the dye is lost during coupling resulting in only a residual carbonyl group (i.e., "Y" in formulas IV, V and VI).

The coupling reaction is generally conducted by adding a molar amount or a substantial molar excess of the functionalized dye of this invention to a composition containing the solid carrier under conditions whereby the functional group(s) on the dye react with a surface reactive group on the solid support. The amount of functionalized dye added in conjunction with the number of reactive sites on the solid support dictates the number of functionalized dye substituents attached to each solid support. In general, sufficient functionalized dye is added so as to provide at least 1 dye substituent per solid support. Preferably, the number of dye substituents is from 1 to about 100 per each solid support.

The resulting solid support having one or more dye substituents bound thereto through a stable covalent bond are particularly useful for providing non-bleeding pH indicators which can have a variety of uses. For example, if the solid supports have particles sizes which form a substantially stable suspension in an aqueous solution, the pH of an incubation, a chemical reaction, etc. can be continuously monitored on-line. Additionally, after incubation, reaction, etc., the particles can be readily removed by centrifugation. Alternatively, the solid support having one or more dye substituents bound thereto can be used as a non bleeding pH indicator incorporated into solid phase pH detection devices such as fibre optic pH sensors. Other uses for these solid phase pH indicators will be readily apparent to those skilled in the art.

The following examples are offered to illustrate this invention and are not to be construed in any way as limiting the scope of this invention.

EXAMPLES

Routinely, reaction courses and product mixtures were monitored by thin layer chromatography using Baker-flex silica gel IB-F sheets. Plates were visualized by iodine vapor or UV light. Ultraviolet-visible (UV-VIS) spectra were recorded with a HP 8452 diode array spectrophotometer. All chemicals were purchased from Aldrich Chemical Company or Sigma and used without further purification. SEPHAROSE™ gels were bought from Pharmacia. Aminoethyl cellulose and aminopropyl silica were obtained from Serva Feinbiochemica while controlled pore glass was purchased from CPG, Inc.

Example 1A—Preparation of Nitro-Phenolphthalein 2 g (10.3 mmol) of 3-nitrophthalic anhydride (Aldrich, order number 15,688-4) were ground in mortar and pestle and placed into an 80 ml beaker. Phenol (22.7 mmol) was added and the beaker was heated in a water bath with stirring. Zinc chloride (0.7 g) was added in small portions. The reaction beaker was then alternately heated in water bath or direct heat to the stated temperature and time. After cooling, the solidified residue was treated with a solution of 30 ml water containing 2 ml concentrated HCl. The solid was broken apart and collected on a glass frit. (If difficulty was encountered, the material could be dissolved in base and then precipitated with concentrated HCl.) The material was placed in a petri dish and allowed to air-dry in a hood overnight. The product of this example was then recovered as a deeply colored powder.

Examples 1B–1E—Preparation of Substituted Nitro-PhenolPhthaleins

Following the procedures set forth in Example 1A, the substituted nitro-phenolphthaleins set forth in Table I and having the following formula were prepared:

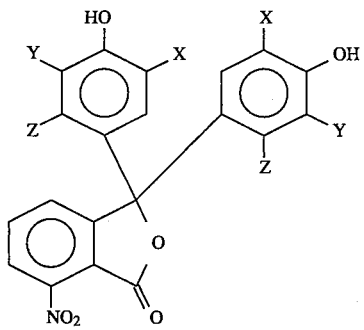

TABLE 1

| | Preparation of Nitro-phthaleins | | | | |
|---|---|---|---|---|---|
| Exp. No. | X | Y | Z | Reaction Conditions | Yield |
| 1A | H | H | H | 180°, 75 minutes | 74% |
| 1B | CH$_3$ | H | CH$_3$ | 110–20°, 60 minutes | 51% |
| 1C | Br | H | H | 115°, 10 minutes | 43% |
| | | | | 75°, 20 minutes | — |
| 1D | Cl | H | H | 80–130°, 40 minutes | 50% |
| 1E | H | H | (C$_6$H$_4$) | 65–70°, 60 minutes | 98% |

Examples 2A–2E—Preparation of Amino-PhenolPhthaleins

The nitro-phenolphthaleins of Examples 1A–1E were converted to amino-phenolphthaleins by the following general procedure:

Combine the appropriate nitro-phthalein (2.3 mmol) and 10 ml of ethyl acetate/t-butanol (9:1) in a round-bottomed flask. Add 2.3 g (10.5 mmol) of SnCl$_2$.2H$_2$O and heat to 60°

C. with stirring for 1 hr. Then add 40 mg of sodium borohydride and continued heating at 65° for 2 hr. After cooling reaction flask, add some water and adjust the pH to about pH 7 with saturated bicarbonate. Filter the solution and after separation of the layers, wash the organic phase with brine and then dry the organic layer with $NaSO_4$. Strip the solvent in vacuo to provide for the desired amino-phenolphthalein as an oily product which sometimes crystallized.

Table 2 below sets forth the various amino-phenolphthaleins prepared from the above general procedure wherein these compounds are represented by the formula:

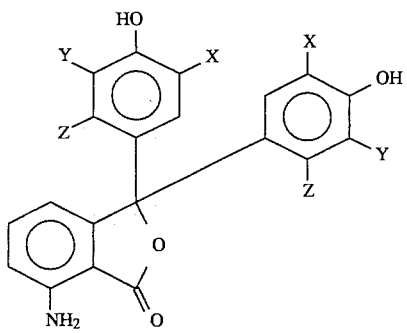

TABLE 2

| Preparation of Amino-phthaleins, 2A–2E | | | | |
|---|---|---|---|---|
| Exp. No. | X | Y | Z | Yield |
| 2A | H | H | H | 26% |
| 2B | $CH_3$ | H | $CH_3$ | 41% |
| 2C | Br | H | H | 26% |
| 2D | Cl | H | H | 22% |
| 2E | H | ($C_6H_4$) | | 60% |

Example 3—Coupling of Amino-PhenolPhthaleins to a Solid Support

The amino-phenolphthaleins of Examples 2A–2E were reacted with a solid support by the following general procedure:

Place 0.5 g of SEPHAROSE™ 6B (commercially available from Pharmacia Inc., Piscataway, N.J. as order number 17-0480-01) into deionized water for 30–45 min. to swell. Collect the white gel. In reaction beaker, place 0.3–0.5 g of an appropriate amino-phthalein into 3 ml dioxane and 20 ml of carbonate buffer (pH 10.5). Add the gel and let sit at 35° for 20 hrs. collect the gel on a glass frit and wash with water, ethanol, acetone and high and low pH buffers. Dialyze the gel against deionized water for 2 days. The resulting support is usually visibly colored which indicates that a covalent bond has formed between the amino group of the amino-phenolphthalein and the epoxide of the SEPHAROSE™ 6B.

Of the amino-phenolphthaleins employed, compounds 2A, 2B and 2E were successfully bound to the SEPHAROSE™ 6B and SEPHAROSE™ 6B bound with compounds 2A and 2B had $pK_a$'s of approximately 10 and 12 respectively.

On the other hand, while compounds 2C and 2D also became bound to the support, these compounds were bound in such a way that they no longer retained their dye properties. Without being limited to any theory, it is believed that the presence of bromine and/or chlorine on the phenolic rings made the phenolic hydrogens more acidic and that the conditions of coupling permitted the solid support to bind through both the phenolic group and the amino group. Binding through the phenolic group destroys the pH dye capacity of the compound because the dye is no longer able to protonate/dedeprotonate.

However, it is contemplated that these functionalized dyes (Compounds 2C and 2D) can be bound to SEPHAROSE™ 6B via another reactive route or alternatively, to another solid support. In the event that these dyes cannot be bound to any solid support without loss of their ability to act as pH dyes, then the chloro and bromo substituents are deemed incompatible substituents when used in combination with an amine substituent as in Compounds 2C and 2D.

Examples 4A–4J—Preparation of Carboxy-PhenolPhthaleins

Several appropriately substituted carboxy-phenolphthalein compounds were prepared by using the following general procedure.

Combine 2 g (10.4 mmol) of 1,2,4-benzenetricarboxylic anhydride (commercially available from Aldrich Chemical Company, Milwaukee, Wis. as order number B440-6) with 22.7 mmol of the appropriate phenol and 0.8 g of zinc chloride in a beaker. Alternately heat the reaction in a water bath or on direct heat to the temperature set forth in Table 3 with stirring. After maintaining these reaction conditions for the time set forth in Table 3, cool the reaction and add a solution of 30 ml water containing 2 ml conc. HCl. Break up and collect the solid residue. After air drying overnight, collect the carboxy-phenolphthalein.

Table 3 below sets forth the various carboxy-phenolphthaleins prepared from the above general procedure (all temperatures are in °C.) and which have the formula

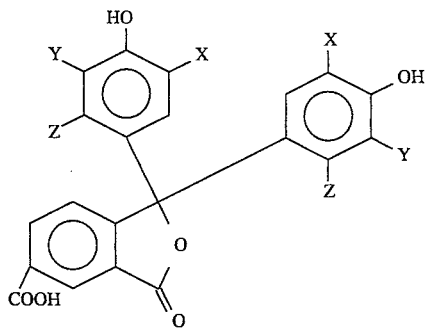

TABLE 3

| Preparation of Carboxy-phenolphthaleins of the formula | | | | | |
|---|---|---|---|---|---|
| Exp. No. | X | Y | Z | Reaction Conditions | Yield |
| 4A | H | H | H | 90–110°, 25 minutes | 33% |
| 4B | Br | H | H | 110°, 20 minutes | 43% |
| 4C | Cl | H | H | 110–130°, 20 minutes | 74% |
| 4D | Cl | Cl | H | 90°, 20 minutes | decomp. |
| 4E | H | ($C_6H_4$) | | 90–120°, 20 minutes | 90% |
| 4F | $NO_2$ | H | H | 100–105°, 25 minutes | 73% |
| 4G | $NO_2$ | H | $NO_2$ | 85–90°, 15 minutes | 88% |
| 4H | Cl | $NO_2$ | H | 80–90°, 15 minutes | 70% |
| 4I | H | OH | H | 90–100°, 20 minutes | 80% |

TABLE 3-continued

Preparation of Carboxy-phenolphthaleins of the formula

| Exp. No. | X | Y | Z | Reaction Conditions | Yield |
|---|---|---|---|---|---|
| 4J | OH | H | $NO_2$ | 90–110°, 25 minutes | 83% |

Example 5—Coupling of Carboxy-PhenolPhthaleins to a Solid Support

The carboxy-phenolphthaleins of Examples 4A–4J were reacted with a solid support by the following general procedure:

Place 0.5 g of SEPHAROSE™ 4B (commercially available from Pharmacia Inc., Piscataway, N.J. as order number 17-0470-01) in 0.5M NaCl for 1 hour and then collect and set aside. Place the appropriate carboxy-phenolphthalein (1.3 mmol) in about 1 ml dimethylformamide and cool to 0° C. in an ice-ethanol bath. Add into this dye solution via a syringe, 0.23 ml (1.8 mmol) isobutyl chloroformate (commercially available from Aldrich Chemical Company, Milwaukee, Wis. as order number 17,798-9) and 0.2 ml (1.8 mmol) N-methyl-morpholine (commercially available from Aldrich Chemical Company as order number M5,655-7). Leave the reaction at this cold temperature for 15–20 minutes. Then add the SEPHAROSE™ 4B gel to reaction along with a scoop of benzyltributyl ammonium bromide and 30 ml of borate buffer (pH 9). Place the reaction flask on a shaker overnight at room temperature. Collect the support on a frit and wash with volumes of water, ethanol, acetone and buffered water. Finally, dialyze the support against water for 1–2 days.

The $pK_a$ of the carboxy-phenolphthalein bound to the solid support (SEPHAROSE™ 4B) was determined and are set forth in Table 4 below:

TABLE 4

$pK_a$'s of Bound Carboxy-Phenolphthaleins

| Carboxy-Phenolphthalein | $pK_a$ |
|---|---|
| 4A | 10 |
| 4B | — |
| 4C | — |
| 4D | — |
| 4E | >10 |
| 4F | — |
| 4G | ~4 |
| 4H | ~5.5 |
| 4I | ~7 |
| 4J | ~6 |

In Table 4, those dyes lacking $pK_a$ values showed a very weak color change with pH thus indicating that the combination of substituents employed in these dyes were incompatible when coupled to SEPHAROSE™ 4B. On the other hand, those dyes having $pK_a$ values demonstrate that these dyes nave been successfully bound to SEPHAROSE™ 4B and are suitable for use as pH indicators.

Example 6—Preparation of 2-Sulfoterephthalic acid

A 500 ml 3-neck flask equipped with an air condenser (connected to Drierite tube), stirrer and thermometer, was charged with terephthalic acid (100 g), oleum (190 g, 3.76 mol of 27–33%) and mercury (2.7 g). The light brown solution was stirred at 255°–260° C. for 7 hours. The color of the mixture changed to dark brown. The reaction mixture was cooled overnight to room temperature, a precipitate had formed. The mixture was then poured very slowly and portionwise into a beaker of ice cold water, (132 ml), whereupon a homogenous solution was formed. Upon cooling, a precipitate formed and the whole was allowed to stand for 2 hours. The precipitate was filtered. The solid acid thus obtained was dissolved in 750 ml of hot $H_2O$, charcoal was added and the mixture allowed to reflux for 35 minutes. It was then filtered hot, passed through a pad of celite, and the filtrate was cooled in an ice bath. The solution was saturated with gaseous hydrogen chloride (1 hour) and the product precipitated out. The precipitate was collected by filtration, dried over $P_2O_5$ in a vacuum dessicator for 48 hours (79 g, 53%), and recrystallized 3 times from acetic acid. Further purification was carried out as follows. The material was dissolved in 200 ml of hot acetic acid and allowed to reflux for 30 minutes. It was then filtered hot and the filtrate was stored in a refrigerator overnight. The precipitate which resulted was filtered and dried at room temperature for several hours and then under high vacuum. The dry pale yellow product (61 g, 41%) melted at 244°–249° C. (Lit 254°–258° C.); Rf=0.35 (1 ml acetic acid: 1 ml $H_2O$: 1.5 ml n-BuOH).

Example 7—Preparation of 4-Carboxy-2-sulfobenzoic anhydride

A dry 500 ml 3-neck flask was equipped with a condenser, stirrer and thermometer under a nitrogen atmosphere. The vessel was charged with 2-sulfoterephthalic acid (100 g, 447 mmol) and acetic anhydride (127 ml). The solution was stirred at 100° C. for 4 hours and then cooled to room temperature (the reaction mixture became homogeneous at 90° C.). A precipitate which had begun to form at 76° C. was then collected by filtration at room temperature (25° C.) under a $N_2$ atmosphere. It was washed with methylene chloride (5×200 ml) and dried in dessicator under high vacuum for 24 hours. The dry white product melted at 210°–213° C. (Lit 208°–210° C.); 66.8 g (65%).

Examples 8A–8C—Preparation of Carboxy-sulfonephthaleins

Place 20 mmol of the appropriate phenol and 0.7 g of zinc chloride into a beaker and warm in a water bath to about 90° C. At this time, slowly add 2.28 g (10 mmol) of 4-carboxy-o-sulfobenzoic anhydride with stirring. Continue to warm the beaker in the water bath or on direct heat to the temperature and time set forth in Table 5 below. Usually a dark mass forms. Cool the reaction and dissolve in 50 ml of 10% NaOH solution. Then add 12 ml of conc. HCl and allow the mixture to sit several hours while the dye product crystallizes out of solution. Collect a darkly colored product and air-dry overnight.

Table 3 below sets forth the various carboxy-phenolphthaleins prepared from the above general procedure (all temperatures are in °C.) and which have the formula

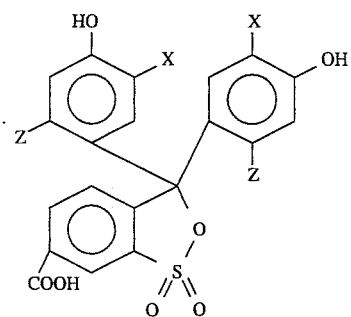

TABLE 5

Carboxy-sulfonephthaleins Prepared per Ex. 8

| Ex. No. | X(ortho) | Z(meta) | Reaction Conditions | Yield |
|---------|----------|---------|---------------------|-------|
| 8A | H | H | 100–110°, 25 minutes | 40% |
| 8B | Cl | H | 140–145°, 40 minutes | 10% |
| 8C | isopropyl | CH$_3$ | 90–110°, 30 minutes | 46% |

Example 9—Coupling of
Carboxy-sulfonephthaleins to Aminoethyl Cellulose

The carboxy-sulfonephthaleins of Examples 8A–8C were reacted with a solid support by the following general procedure:

Place 0.5 g aminoethyl cellulose (commercially available from Serra Biochemicals, Westbury, N.Y. 11590 as order no. 45015) in 30 ml of deionized water and set aside. Place 0.2 g of an appropriate dye in 25 ml of pyridine-HCl buffer (pH 5.8). Add the filtered cellulose to this reaction along with 83 mg of N-ethyl-N'-(3-dimethylaminopropyl)carbodiimide hydrochloride (EDC). Place the reaction on a shaker overnight at room temperature. Collect the support and wash with large volumes of water, ethanol, acetone, DMF and pH buffers over the course of 2 days. Collect a final colored support. Also, this same procedure was run using aminopropyl silica beads (Serva #43660) in place of cellulose.

The pK$_a$'s of the carboxy-sulfonephenolphthaleins bound to the solid support (aminoethyl cellulose) was determined and are set forth in Table 4 below:

TABLE 4 pK$_a$'s of Bound Carboxy-sulfonephthaleins

| Carboxy-Phenolphthalein | pK$_a$ |
|-------------------------|--------|
| 8A | 7.6 |
| 8B | 6.2 |
| 8C | 9.2 |

By following the procedures set forth above, other functionalized dyes can likewise be prepared by merely substituting one reagent for another. For example, as shown above, different Ar groups on the dye can be prepared by substituting phenol or 1-naphthol having from 0 to 3 substituents as defined above. Likewise, appropriately substituted phthalic anhydride (or its corresponding naphthlenic anhydride) can be employed by mere substitution for phthalic anhydride in the above examples. Additionally, appropriately substituted o-sulfobenzoic anhydrides (or its corresponding o-sulfonaphthalenic anhydride) can be employed by mere substitution for p-carboxy-o-sulfobenzoic anhydride described above.

What is claimed is:

1. A solid support having one or more dye substituents attached thereto which support is represented by formula IV, V or VI:

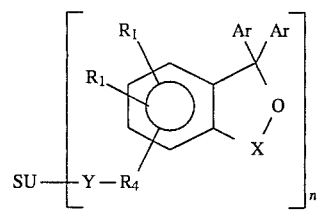

IV

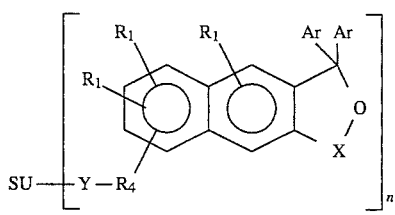

V and

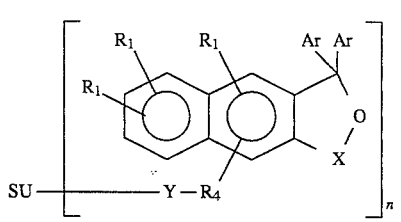

VI wherein each R$_1$ is independently hydrogen or a compatible substituent selected from the group consisting of hydrogen, alkyl groups of from 1 to 6 carbon atoms, and alkoxy groups of from 1 to 6 carbon atoms; R$_4$ is a covalent bond or a compatible linker group selected from the group consisting of hydrocarbyl groups and carbonylhydrocarbyl groups; SU is a solid support; Y is the residue of the reactive functionality attached to R$_4$ selected from the group consisting of carboxylic acid groups, amine groups, hydroxyl groups, unsaturted aliphatic groups and epoxides and which forms a stable covalent bond with the solid support; each Ar is independently a 4-hydroxyphenyl or 4-hydroxynaphthyl group having from 0 to 3 compatible substituents selected from the group consisting of alkyl of from 1 to 6 carbon atoms, halo and nitro and n is an integer equal to at least 1.

2. A solid support as described in claim 1 wherein each R$_1$ is hydrogen.

3. A solid support as defined in claim 1 wherein R$_4$ is a bond or group defined by the formula $$-[C(O)]_p(NR_6)_qR_7-(Y)_s$$

wherein Y is as defined above, p is an integer equal to zero or one; q is an integer equal to zero or one; R$_6$ is hydrogen or a hydrocarbyl group of from 1 to about 10 carbon atoms; R$_7$ is a hydrocarbyl group of from 1 to about 10 carbon atoms; and s is an integer equal to at least 1.

4. A solid support as defined in claim 3 wherein Y is selected from the group consisting of carbonyl or amino.

5. A solid support of the formula:

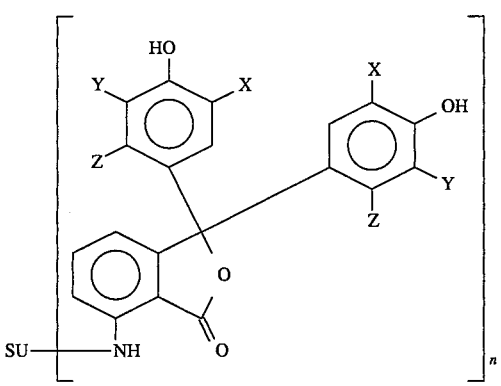

wherein X, Y and Z are independently hydrogen or methyl or Y and Z are linked to form a second phenyl ring so as to form a napthyl substituent; SU is a solid support; and n is an integer equal to at least 1.

6. A solid support according to claim 5 wherein X, Y and Z are hydrogen and SU is agarose gel.

7. A solid support according to claim 5 wherein each X and Z is methyl, each Y is hydrogen and SU is agarose gel.

8. A solid support according to claim 5 wherein each X is hydrogen, Y and Z are a second phenyl ring so as to form a naphthyl substituent and SU is agarose gel.

9. A solid support of the formula:

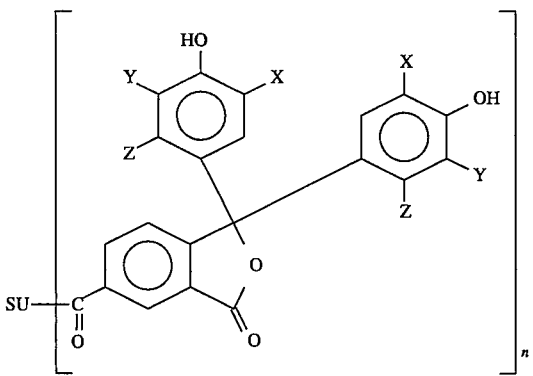

wherein SU is a solid support; and n is an integer equal to at least 1; and X, Y and Z are independently selected from the group consisting of hydrogen, hydroxyl, chloro, bromo, or Y and Z are linked to form a second phenyl ring so as to form a naphthyl substituent with the proviso that if Y and Z are hydrogen, then X is not bromo, chloro or nitro and with the further proviso that if Z is hydrogen, then X and Y are not both chloro.

10. A solid support as defined in claim 9 wherein each of X, Y and Z is hydrogen and SU is agarose gel.

11. A solid support as defined in claim 9 wherein said X is hydrogen and Y and Z are a second phenyl ring so as to form a naphthyl substituent and SU is agarose gel.

12. A solid support as defined in claim 9 wherein each X and Z is nitro and each Y is hydrogen and SU is agarose gel.

13. A solid support as defined in claim 9 wherein each X is chloro, each Y is nitro and each Z is hydrogen and SU is agarose gel.

14. A solid support as defined in claim 9 wherein each X and Z is hydrogen and each Y is hydroxyl and SU is agarose gel.

15. A solid support as defined in claim 9 wherein each X is hydroxyl, each Y is hydrogen and each Z is nitro and SU is agarose gel.

16. A solid support of the formula:

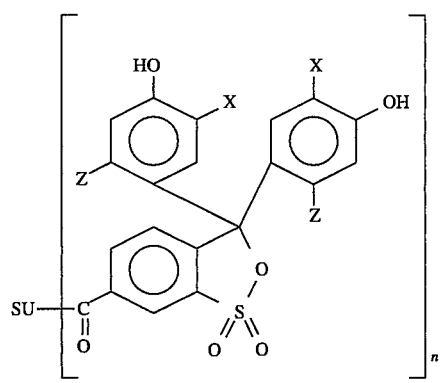

wherein X and Z are independently selected from the group consisting of hydrogen, chloro, bromo, and alkyl of from 1 to 6 carbon atoms, SU is a solid support and n is an integer equal to at least 1.

17. A solid support as defined in claim 16 wherein each of X and Z is hydrogen and SU is aminoethylcellulose.

18. A solid support as defined in claim 16 wherein each X is chloro and each Z is hydrogen and SU is aminoethylcelluose.

19. A solid support as defined in claim 16 wherein each X is isopropyl and each Z is methyl and SU is aminoethylcellulose.

* * * * *